United States Patent
Zhang et al.

(10) Patent No.: US 10,932,865 B2
(45) Date of Patent: Mar. 2, 2021

(54) PRECISION DETECTION METHOD AND DEVICE FOR SURGICAL ROBOT POSITIONING SYSTEM

(71) Applicant: Tinavi Medical Technologies Co., Ltd., Beijing (CN)

(72) Inventors: Weijun Zhang, Beijing (CN); Yinyan Li, Beijing (CN); Weiyan Kong, Beijing (CN)

(73) Assignee: TINAVI MEDICAL TECHNOLOGIES CO., LTD., Beijing (CN)

( * ) Notice: Subject to any disclaimer, the term of this patent is extended or adjusted under 35 U.S.C. 154(b) by 0 days.

(21) Appl. No.: 16/560,227

(22) Filed: Sep. 4, 2019

(65) Prior Publication Data
US 2020/0163725 A1 May 28, 2020

(30) Foreign Application Priority Data
Nov. 23, 2018 (CN) .......................... 201811409733.5

(51) Int. Cl.
  *A61B 34/20* (2016.01)
  *A61B 34/30* (2016.01)
  *G01B 11/03* (2006.01)

(52) U.S. Cl.
  CPC .............. *A61B 34/20* (2016.02); *A61B 34/30* (2016.02); *G01B 11/03* (2013.01); *A61B 2034/2055* (2016.02); *A61B 2034/2065* (2016.02); *G05B 2219/39011* (2013.01)

(58) Field of Classification Search
  CPC .............. A61B 34/20; A61B 34/30–37; A61B 2034/2055; A61B 2034/207; A61B 2034/301–306; B25J 9/1692; G05B 2219/39019; G05B 2219/39024; G05B 2219/39026; G05B 2219/39032; G05B 2219/39041; G05B 2219/39047; G05B 2219/39011; G05B 2219/39021
  See application file for complete search history.

(56) References Cited

U.S. PATENT DOCUMENTS

2016/0346930 A1\* 12/2016 Hares ..................... B25J 9/1679
2018/0194010 A1\* 7/2018 Huang .................. B25J 9/1692

\* cited by examiner

*Primary Examiner* — Spencer D Patton
(74) *Attorney, Agent, or Firm* — Panitch Schwarze Belisario & Nadel LLP

(57) ABSTRACT

A precision detection method for detecting the precision of a surgical robot positioning system includes: acquiring spatial position coordinates of a first detection point and a second detection point; acquiring information of a spatial axis for a surgical robot reaching a planned path, wherein the planned path is formed based on the first detection point and the second detection point; and calculating a first distance from the first detection point to a spatial axis and a second distance from the second detection point to the spatial axis. The precision detection method for a surgical robot positioning system can accurately detect the precision of the surgical robot positioning system.

9 Claims, 5 Drawing Sheets

PRECISION DETECTION METHOD AND DEVICE FOR SURGICAL ROBOT POSITIONING SYSTEM

CROSS-REFERENCE TO RELATED APPLICATIONS

This application claims priority under 35 U.S.C. § 119(b) to Chinese Patent Application No. 201811409733.5, filed Nov. 23, 2018, which is incorporated herein by reference in its entirety.

BACKGROUND OF THE INVENTION

1. Technical Field

The invention relates to the field of medical instruments, and in particular, to a precision detection method and device for a surgical robot positioning system.

2. Description of Related Art

Surgical operations based on surgical robots have become more and more popular. When a robot is used for positioning (positioning of surgical instruments or implants) during surgery, the positioning precision of the robot is an important indicator that determines the success of the surgery. It is a critical task for ensuring safe and smooth proceeding of the surgery to correctly evaluate the positioning precision of the robot positioning system. Nowadays, major indicators that are adopted to evaluate the positioning precision of the surgical robot positioning system comprise absolute precision and repeated positioning precision.

During actual surgery, the most important role that a surgical robot plays is to determine a surgery path that can be described with a spatial straight line. The precision requirements for a surgical robot system not only include the point positioning error requirement, but also include the point positioning and the orientation error requirements, and in certain cases, the orientation requirement is even more important. Thus, the precision of the surgical robot cannot be comprehensively evaluated by absolute precision and repeated positioning precision which simply express point positioning errors. In practice, however, accurate measurement of the point-to-point distance in space is very difficult.

BRIEF SUMMARY OF THE INVENTION

The invention provides a precision detection method and device for a surgical robot positioning system to solve the problem of difficult detection of the precision of a surgical robot positioning system.

On the one hand, the invention provides a precision detection method for a surgical robot positioning system, wherein the precision detection method is used for detecting the precision of the surgical robot positioning system and comprises the following steps:

Acquiring spatial position coordinates of a first detection point and a second detection point;

Acquiring information of a spatial axis for a surgical robot reaching a planned path, wherein the planned path is formed based on the first detection point and the second detection point; and Calculating a first distance from the first detection point to the spatial axis and a second distance from the second detection point to the spatial axis.

In one embodiment of the invention, the acquiring spatial position coordinates of a first detection point and a second detection point comprising: acquiring the spatial position coordinates of the first detection point and the second detection point measured with a three-dimensional measurement instrument.

In one embodiment of the invention, the acquiring information of a spatial axis for a surgical robot reaching a planned path comprises the following steps:

Acquiring a scan image of the first detection point and the second detection point in the surgical robot positioning system;

Forming the planned path by taking imaging points of the first detection point and the second detection point in the scan images respectively as an In point and an Out point; and Acquiring the information of the spatial axis for the surgical robot moving to planned path.

In one embodiment of the invention, the precision detection method further comprises the step of carrying out image registration on the scan images and the first and second detection points after the scan image has been acquired.

In one embodiment of the invention, the precision detection method further comprises the following step:

Acquiring position information of the first detection point and the second detection point at a certain frequency, and adjusting the planned path when the position information of the detection points changes.

In one embodiment of the invention, the acquiring the information of the spatial axial of the planned path for the surgical robot moving to the planned path comprises: acquiring the information of the spatial axis by measuring central axis information of a test probe at an execution end of the surgical robot.

In one embodiment of the invention, the central axis information of the test probe at the execution end of the surgical robot is measured through a three-dimensional measurement instrument.

In one embodiment of the invention, the central axis information of the test probe at the execution end of the surgical robot is measured through the following steps:

Acquiring coordinates of at least two fitting points on the central axis of the test probe; and Fitting the coordinates of the at least two fitting points to obtain the position of the central axis of the test probe.

In one embodiment of the invention, the acquiring coordinates of at least two fitting points on a the central axis of the test probe comprises taking central holes at two ends of the test probe respectively as a first fitting point and a second fitting point, to obtain a coordinate $P1(x_1, y_2, z_1)$ of the first fitting point, and a coordinate $P2(x_2, y_2, z_2)$ of the second fitting point.

In one embodiment of the invention, the coordinate of the first detection point is $Xa(x_a, y_a, z_a)$, and the coordinate of the second detection point is $Xb(x_b, y_b, z_b)$;

The calculating a first distance from the first detection point to the spatial axis and a second distance from the second detection point to the spatial axis comprise calculating the first distance and the second distance according to the following formula:

$$L_i = \sqrt{[(x_1 - x_i) + (x_2 - x_1)t]^2 + [(y_1 - y_i) + (y_2 - y_1)t]^2 + [(z_1 - z_i) + (z_2 - z_1)t]^2},$$

-continued $$\text{wherein, } t = -\frac{(x_1 - x_i)(x_2 - x_1) + (y_1 - y_i)(y_2 - y_1) + (z_1 - z_i)(z_2 - z_1)}{(x_2 - x_1)^2 + (y_2 - y_1)^2 + (z_2 - z_1)^2};$$

i is a or

La is the first distance, and Lb is the second distance.

In one embodiment of the invention, the test probe has a length of 50-150 mm.

In one embodiment of the invention, the precision detection method further includes the following step:

Selecting two detection points from a plurality of detection points except the first and second detection points to carry out precision detection again.

In the other aspect, the invention provides a precision detection device for a surgical robot positioning system, wherein the precision detection device is used for detecting the precision of a surgical robot positioning system and comprises:

a base;

two or more props each having a first end and a second end opposite to the first end, wherein the first end is connected to the base; and two or more X ray-proof detection points arranged at the second ends of the props in a one-to-one correspondence manner.

In one embodiment of the invention, the detection points have a diameter of 2.5-3.5 mm.

In one embodiment of the invention, the precision detection device further comprises:

a plurality of X ray-proof registration reference points arrayed on the base in a preset manner.

In one embodiment of the invention, the registration reference points have a diameter of 1.0-2.0 mm.

In one embodiment of the invention, the precision detection device further includes:

a tracer fixed to the base and used for indicating the spatial position of the base.

In one embodiment of the invention, the tracer comprises:

A support; and

Three or more markers arranged on the support, wherein at least one marker is not collinear with the other markers.

In one embodiment of the invention, the base has an installation surface provided with two or more installation holes, and the first ends of the props are detachably connected to the installation holes.

In one embodiment of the invention, the props are perpendicular to the installation surface, and the two or more props include a first set of props arranged in pair, a second set of props arranged in pair, and a third set of props arranged in pair, the props in the first set respectively have a length of 80-90 mm and a length of 20-30 mm, the props in the second set respectively have a length of 45-55 mm and a length of 20-30 mm, and the props in the third set respectively have a length of 20-30 mm and a length of 20-30 mm.

In one embodiment of the invention, the two or more installation holes are distributed in an array manner, an inter-row distance between the two or more installation holes is 50-70 mm, and an inter-column distance between the two or more installation holes is 20-40 mm.

In one embodiment of the invention, the installation holes have a diameter of 5-8 mm and a depth of 5-8 mm;

the props are hollow props, connectors matched with the installation holes are arranged at one ends of the props, the props have an outer diameter of 5-8 mm and an inner diameter of 4-7 mm, and the connectors have an outer diameter of 5-8 mm and extend outwards by 5-8 mm from one ends of the props.

In one embodiment of the invention, the installation surface is a top surface of the base, is rectangular, and has a first edge and a second edge adjacent to the first edge, wherein the first edge has a length of 80-100 mm, the second edge has a length of 100-120 mm, and the base has a height of 70-90 mm.

According to the precision detection method for a surgical robot positioning system of the invention, a preset path is planned based on the first detection point and the second detection point, the test probe is arranged on the path, the first distance from the first detection point to the central axis of the test probe and the second distance from the second detection point to the central axis of the test probe are acquired to figure out the system precision of the surgical robot at the first detection point and the second detection point, and thus, accurate detection of the precision of the surgical robot system is realized. Precision detection at multiple detection points can be completed through one time of position scanning, calibrating registration and path planning, so that the detection efficiency of the precision of the surgical robot system is improved.

BRIEF DESCRIPTION OF THE DRAWINGS

Those skilled in the art can appreciate other characteristics, objectives, and advantages of the invention by reading the detailed description of non-restrictive embodiments with reference to the following accompanying drawings, wherein identical or similar reference signs in the drawings represent identical or similar features.

DETAILED DESCRIPTION OF THE INVENTION

The various characteristics and illustrative embodiments of the invention are detailed below. For a better understanding of the objectives, technical solutions, and advantages of the invention, the invention is further described below with reference to the accompanying drawings and embodiments. It should be understood that the embodiments in the following description are only used to explain the invention, and are not intended to limit the invention. Those skilled in the field can implement the invention without some of these specific details. These illustrative embodiments in the following description are merely used to fulfill a better comprehension to the invention.

What should be pointed out is that the relational terms such as "first" and "second" in this description are only used to distinguish one entity or operation from another, and do not require or imply that these entities or operations have any actual relationships or are configured in any sequences. In addition, the terms such as "include", "include", or any other variations thereof refer to non-exclusive inclusion, which means that a process, method, article, or device including a series of elements not only includes these elements listed, but also includes other elements that are not explicitly listed, or further includes inherent elements of this process, method, article, or device. Only otherwise specifically limited, the process, method, article, or device referred to not only includes the elements defined by the term "include", but also may include other similar elements.

It should be understood that, when describing the structure of a component, one layer or area being located "on" or "above" another one may indicate that one layer or area is directly located on another one, or indicate that other layers or areas exist between these two layers or areas. Moreover, if this component is flipped, this layer or area will be located "under" or "below" the another one.

Figure 1:
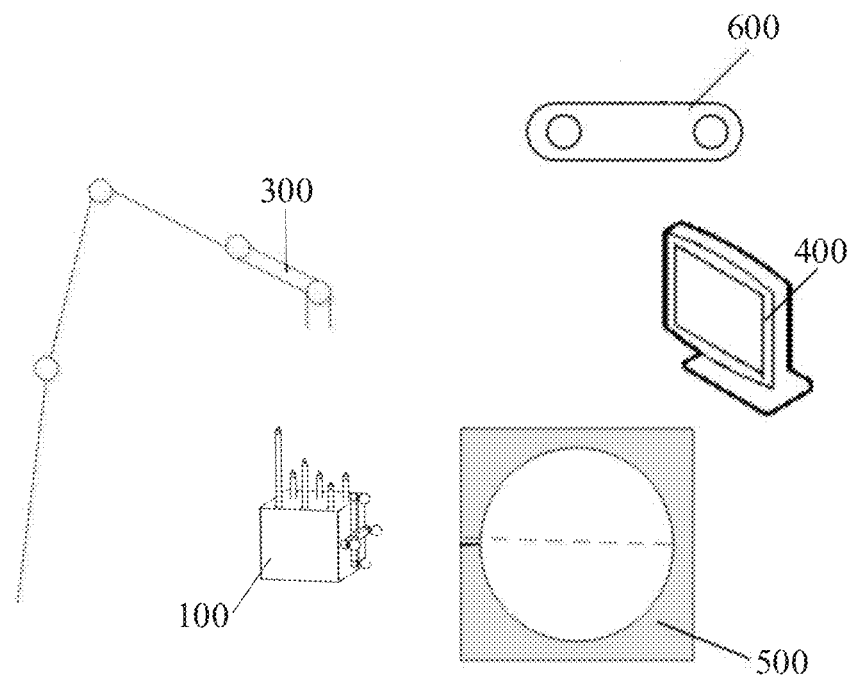
FIG. 1 is a structural diagram of a surgical robot positioning system.

This embodiment of the invention provides a precision detection method for a surgical robot positioning system, and the precision detection method is used for detecting the precision of a surgical robot positioning system, FIG. 1 is a structural diagram of the surgical robot positioning system. The precision detection method can detect the precision of a positioning system including a surgical robot 300, an upper computer 400, and an imaging device 500 (the imaging device 500 is a two-dimensional or a three-dimensional imaging device, and the three-dimensional imaging device is adopted in this embodiment), and can also detect the precision of a positioning system having more functions, such as the surgical robot positioning system including a surgical robot 300, an upper computer 400, an imaging device 500, and an optical tracker 600, as shown in FIG. 1. The surgical robot 300 can be provided with a tracer. As shown in FIG. 1, when precision detection of the positioning system is completed, a detection device 100 is positioned within the imaging range of the imaging device 500 for image acquisition, so that corresponding scan images of the detection device 100 are acquired. Corresponding precision detection systems can be formed for different positioning systems.

Figure 2:
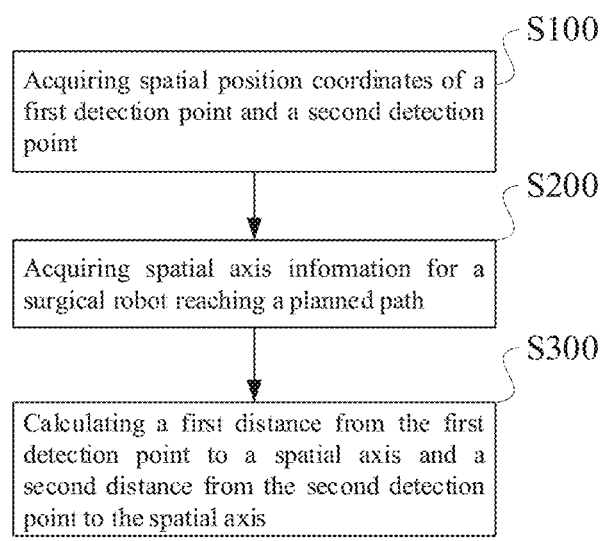
FIG. 2 is a flow diagram of a precision detection method for a surgical robot positioning system according to an embodiment of the invention.

FIG. 2 is a flow diagram of the precision detection method for a surgical robot positioning system according to an embodiment of the invention. As shown in FIG. 2, the precision detection method includes the following steps from S100 to S300:

In step S100, spatial position coordinates of a first detection point and a second detection position are acquired. The first detection point and the second detection point are selected from a plurality of detection points, wherein the first detection point and the second detection point are detection points located on a preset precision detection device 100 for a surgical robot positioning system. The precision detection device 100 is arranged in an effective work space of a surgical robot 300, and the precision detection device 100 for a surgical robot positioning system will described in detail below. In this embodiment, the coordinate of the first detection point is $Xa(x_a, y_a, z_a)$, and the coordinate of the second detection point is $Xb(x_b, y_b, z_b)$.

In this embodiment, in the step of acquiring the spatial position coordinates of the first detection point and the second detection point, the spatial position coordinates of the first detection point and the second detection point are measured through a three-dimensional measurement instrument.

The detection device 100 is arranged within the imaging range of the three-dimensional imaging device 500 for scanning, and the three-dimensional imaging device 500 acquires images of the detection device 100 (the images of the detection device 100 include images of detection points and may also include images of registration reference points) and then transmits the images to the upper computer 400. The refrigeration reference points are configured on the detection device 100 to complete image registration, or an independent positioning device with registration points is used to complete image registration. This description is described by the example of the detection device 100 being configured with registration reference points. Furthermore, the detection device can be provided with a tracer, and while implementing three-dimensional scanning on the detection device 100, the optical tracker 600 acquires the coordinates of the tracer and then transmits the coordinates of the tracer to the upper computer 400, so that real-time tracking is realized.

S200, information of a spatial axis for the surgical robot 300 reaching a planned path is acquired, wherein the planned path is formed based on the first detection point and the second detection point.

In steps S100 and S200, the spatial position coordinates of the detection points and the information of a spatial axis can be acquired through one test device such as a three-dimensional measurement instrument, so that data acquired in step S100 and step S200 are in the same coordinate system. Data detected by the test device are then transmitted to the upper computer 400.

Figure 3:
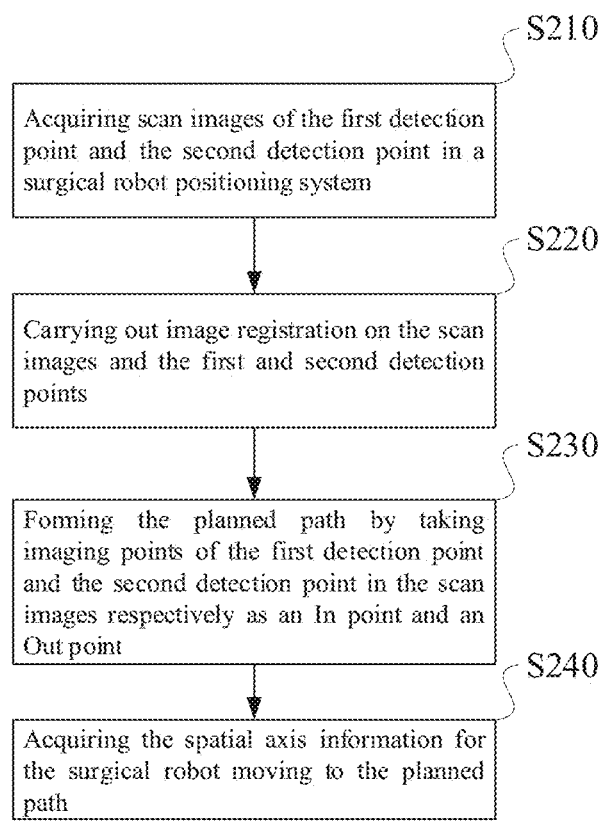
FIG. 3 is a flow diagram of the step of acquiring information of a spatial axis for a surgical robot reaching a planned path according to the detection method according to an embodiment of the invention.

FIG. 3 is a flow diagram of the step of acquiring the information of a spatial axis for the surgical robot to reach the planned path according to the detection method of the invention. As shown in FIG. 3, step S200 specifically includes the following steps from S210 to S240:

In step S210, scan images of the first detection point and the second detection point in the surgical robot 300 positioning system are acquired.

In step S220, image registration is carried on the scan images and the first and second detection points.

The registration process can comprise: the upper computer 400 compares geometrical characteristics of the registration reference points in the images with that of a preset positioning point, so that the registration reference points in the detection device 100 and the positioning reference points in the images are correspondingly recognized.

In step S230, the planned path is formed by taking imaging points of the first detection point and the second detection point in the scan images respectively as an In point and an Out point.

In this embodiment, the first detection point and the second detection point are selected from the registered images to respectively serve as an In point and an Out point to form the planed path; and under different operation conditions, two points can be selected from the images, and then the spatial coordinates of the corresponding detection points are measured.

In some embodiments, after registration, either the coordinate system of the images or the coordinate system of the detection device 100 is regarded as a world coordinate system, and in this case, the spatial coordinates of the planned path are expressed as a straight line in the world coordinate system, and the straight line is output as the planned path;

As mentioned above, the surgical robot 300 positioning system may further include the optical tracker 600 for tracking other devices in real time. In order to ensure the accuracy of precision detection, the spatial position of the detection device 100 can be monitored in real time, so as to prevent inaccurate precision detection caused by position changes. On this basis, the precision detection method further includes acquiring position information of the first detection point and the second detection point and adjusting the planned path when the position information of the detection points changes.

In this process, the optical tracker 600 having a real-time tracking function monitors the movement of the detection device 100 in real time (namely, monitoring the tracer on the detection device 100), calculates the moving direction and distance of the detection device 100, and transmits the moving direction and distance of the detection device 100 to the upper computer 400. The upper computer 400 controls the surgical robot 300 to correct self movement according to the moving direction and distance, so as to make sure that a guider moves exactly along the planned path. In order to realize real-time monitoring, the optical tracker 600 can refresh monitoring data at a certain frequency.

In step S240, the information of a spatial axis for the surgical robot 300 moving to the planned path is acquired.

In this embodiment, in the step of acquiring the information of a spatial axis for the surgical robot 300 moving to the planned path, the central axis information of an execution end of the surgical robot 300 is acquired to serve as the information of a spatial axis. In another embodiment, a test probe is installed at the execution end to acquire the central axis information.

In this embodiment, a guide device is arranged at the execution end of the surgical robot 300, and the test probe is installed on the guide device of the surgical robot 300. After the planned path has been worked out, the upper computer controls the surgical robot 300 to move accurately, so that the guider connected to the tail end of the surgical robot 300 points to the planned path. The central axis of the test probe is the axis of the guider, i.e., the actual navigation position of the surgical robot 300.

Figure 4:
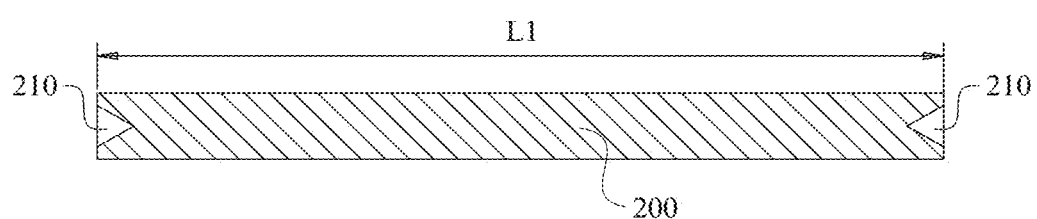
FIG. 4 is a sectional view of a test probe adopted in the precision detection method for a surgical robot positioning system according to an embodiment of the invention.

FIG. 4 is a sectional view of the test probe adopted in the precision detection method for a surgical robot positioning system according to an embodiment of the invention. As shown in FIG. 4, the test probe 200 is columnar and has two ends formed with central holes 210. The test probe 200 has a length L1 of 50-150 mm such as 100 mm, and the length tolerance of the test probe 200 is within 0.05 mm. In consideration of the characteristics of the positioning system, the accuracy of detection data and the space occupancy are kept balanced when the test probe is 100 mm long. In different applications, the diameter of the test probe 200 and the size of the central holes 210 can be designed according to the actual requirement of the surgical robot 300.

In some embodiments, the central axis information of the test probe at the execution end of the surgical robot 300 is measured through a three-dimensional measurement instrument.

In this embodiment, the spatial positions of the detection points and the test probe are detected through the same test device, so that data transmitted to the upper computer 400 are ensured from the same coordinate system, and the test accuracy is ensured.

Specifically, the axis information of the test probe at the execution end of the surgical robot 300 is measured through the following steps: the coordinates of at least two fitting points on the central axis of test probe are acquired, and the coordinates of the at least two fitting points are fitted to obtain the position of the central axis of the test probe.

In the step of acquiring the coordinates of at least two fitting points of the central axis of the test probe, the central holes at the two ends of the test probe are respectively taken as a first fitting point and a second fitting point, the coordinate of the first fitting point is $P1(x_1, y_1, z_1)$, and the coordinate of the second fitting point is $P2(x_1, y_2, z_2)$. In other embodiments, other axial positions of the test probe can be tested to acquire the central axis information.

In step S300, a first distance La from the first detection point to a spatial axis and a second distance Lb from the second detection point to the spatial axis are calculated, wherein the first distance La and the second distance Lb indicate the system precision of the surgical robot 300 at the first detection point and the second detection point.

In this embodiment, in the step of calculating the first distance La from the first detection point to the spatial axis and the second distance Lb from the second detection point to the spatial axis, the first distance La and the second distance Lb are calculated according to the following formula:

$$L_i = \sqrt{[(x_1 - x_i) + (x_2 - x_1)t]^2 + [(y_1 - y_i) + (y_2 - y_1)t]^2 + [(z_1 - z_i) + (z_2 - z_1)t]^2},$$

In the above formula, $$t = -\frac{(x_1 - x_i)(x_2 - x_1) + (y_1 - y_i)(y_2 - y_1) + (z_1 - z_i)(z_2 - z_1)}{(x_2 - x_1)^2 + (y_2 - y_1)^2 + (z_2 - z_1)^2};$$

i is a or b, a or b is substituted to i in the formula to work out La or Lb, La is the first distance, and Lb is the second distance.

In addition, in some embodiments, the precision detection method for a surgical robot positioning system further includes the step of selecting two detection points except the first and second detection points from the plurality of detection points to carry out precision detection again.

In the case where a third detection point, a fourth detection point, a fifth detection point, and a sixth detection point are selected to serve as detection points, the first detection point and the second detection point mentioned above are replaced with the third detection point and the fourth detection point, and then the above steps are repeated to obtain the system precision of the surgical robot positioning system at the third detection point and the fourth detection point; afterwards, the first detection point and the second detection point are replaced with the fifth detection point and the sixth detection point, and then the above steps are repeated to obtain the system precision of the surgical robot positioning system at the fifth detection point and the sixth detection point. Only if the system precision of the surgical robot positioning system at any pair of detection points meets a predeclared requirement, the system precision of the surgical robot positioning system at this point is qualified.

According to the precision detection method for the surgical robot positioning system in this embodiment of the invention, a preset path is planned based on the first detection point and the second detection point, and the test probe is arranged on the path. The first distance La from the first detection point to the central axis of the test probe and the second distance Lb from the second detection point to the central axis of the test probe are acquired to figure out the system precision of the surgical robot positioning system at the first detection point and the second detection point, so that accurate detection of the precision of the surgical robot positioning system is realized. The precision detection at multiple detection points can be completed through one-time position scanning, calibration registration, and path planning, so that the precision detection efficiency of the surgical robot positioning system is improved. In addition, this invention solves the problem in the prior art that the point-line distance is difficult to detect during precision detection, and the detection accuracy of the precision of the positioning system is improved.

This embodiment of the invention further provides a precision detection device 100 for a surgical robot 300 positioning system. The precision detection device is applied to the above precision detection method for a surgical robot 300 positioning system to detect the system precision for the surgical robot 300 at preset detection points. The precision detection device 100 for a surgical robot 300 positioning system includes a base 110, two or more props 120, and two or more X ray-proof detection points 130, wherein each prop 120 has a first end and a second end opposite to the first end. The first end of each prop 120 is connected to the base 110, and the two or more detection points 130 are arranged at the second ends of the props 120 in a one-to-one correspondence manner.

The base 110 may be made from polymethyl methacrylate (PMMA) with a good X-ray transrnissivity, and the props 120 may be hollow and columnar, and may be made from carbon fibers or engineering plastics.

The precision detection device 100 for a surgical robot 300 positioning system in this embodiment of the invention can cooperatively complete accurate detection of the precision of the surgical robot 300 positioning system. A plurality of detection points 130 can be set on the precision detection device 100, and precision detection at the plurality of detection points 130 can be completed through one-time position scanning, calibrating registration and path planning, so that the defection efficiency of the precision of the surgical robot 300 positioning system is improved.

In some embodiments, the X ray-proof detection points 130 are first metal balls such as stainless steel balls, so that sharper medical images can be obtained. The first metal balls have a diameter of 2.5-3.5 mm, such as 3 mm, and the diameter deviation is controlled within 0.02 mm.

In this embodiment, the precision detection device 100 further includes a plurality of X ray-proof registration reference points 140, which are arranged on a preset plane of the base 110 in a preset rule to complete registration. In this embodiment, the registration reference points 140 may be second metal balls, such as stainless steel balls, so that sharper medical images can be obtained. The second metal balls have a diameter of 1.5 mm, and the diameter deviation is controlled within 0.02 mm. The plurality of registration reference points 140 are arranged to integrate a registration scale on the precision detection device 100, facilitating rapid calibration registration for precision detection of the surgical robot 300.

The precision detection device 100 may further include a tracer 150, which is fixed to the base 110 and used for indicating the spatial position of the base 110. In this embodiment, the tracer 150 includes a support 152 and three or more markers 151.

The support 152 includes a center part connected with the base 110, and three or more connection parts extending outwards from the center part. The three or more markers 151 are correspondingly arranged on the connection parts of the support 152, wherein at least one marker 151 is not collinear with the other markers 151. In this embodiment, the support 152 includes four connection parts which are arrayed in a crossed manner, and correspondingly, four markers 151 are arranged at the ends of the four connection parts. In other embodiments, the design of the support can be changed under the premise that the tracer can be recognized.

Figure 5:
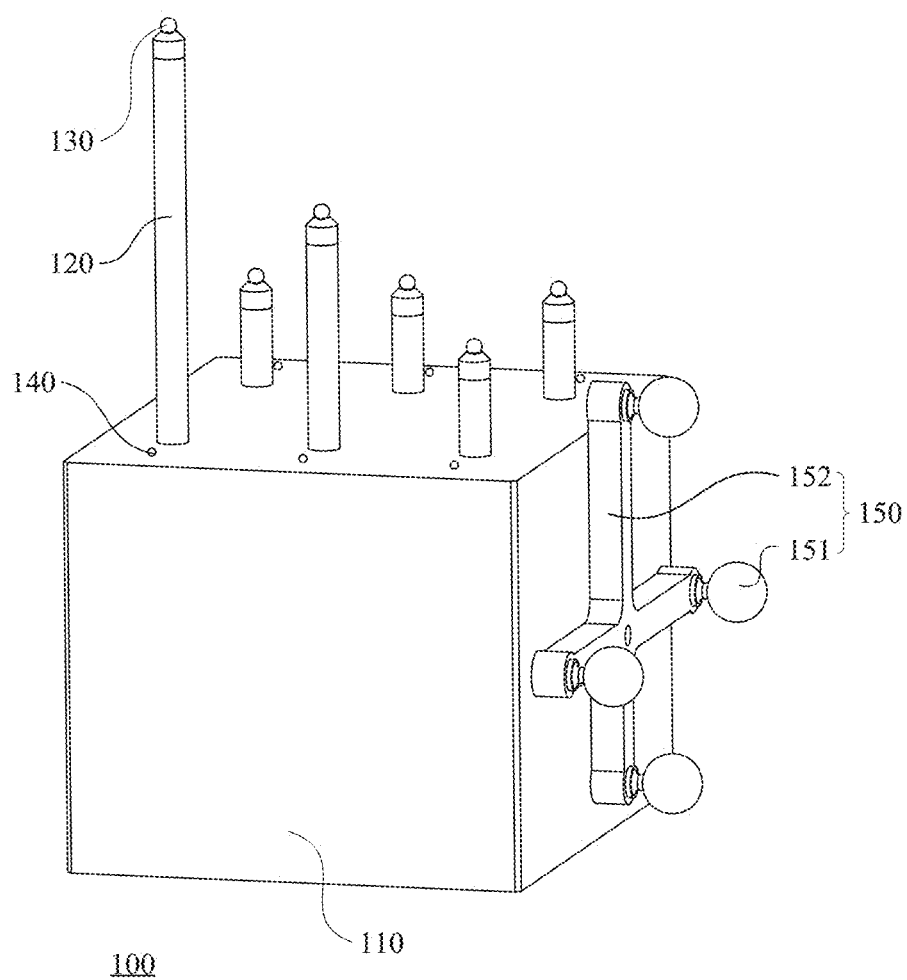
FIG. 5 is a structural diagram of a precision detection device for a surgical robot positioning system according to an embodiment of the invention.
Figure 6:
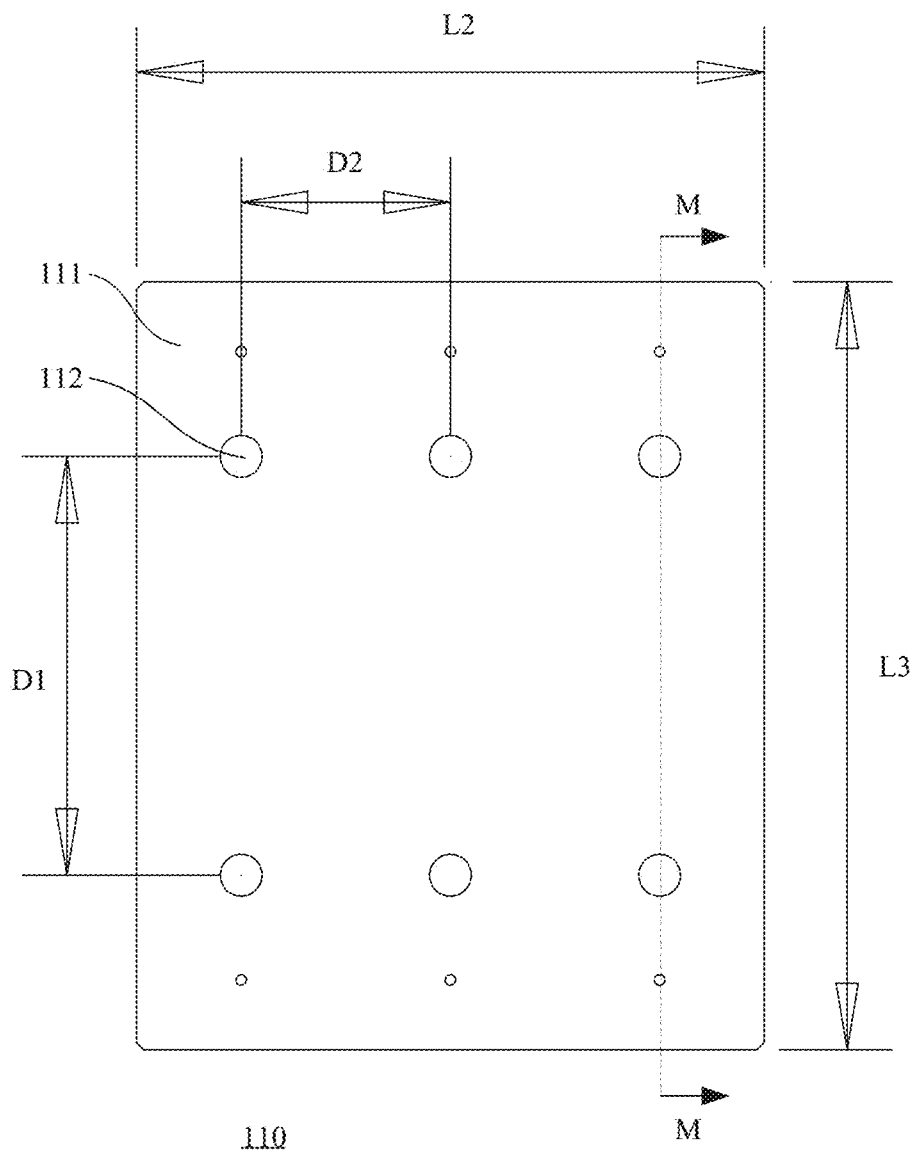
FIG. 6 is a top view of a base of the precision detection device for a surgical robot positioning system according to an embodiment of the invention.

FIG. 5 is a top view of the base 10 of the precision detection device 100 for a surgical robot 300 positioning system of the invention, and FIG. 6 is a sectional view in the MM direction in FIG. 5. The base 110 has an installation surface 111 provided with two or more installation holes 112, and the first ends of the props 120 are detachably connected into the installation holes 112.

The installation surface 111 can be the top surface of the base 110. In this embodiment, the installation surface 111 is rectangular and has a first edge and a second edge adjacent to the first edge, wherein the first edge has a length L2 of 80-100 mm, such as 90 mm, the second edge has a length L3 of 100-120 mm, such as 110 mm, and the base 110 has a height H1 of 70-90 mm, such as 80 mm. In this embodiment, a space is defined in the base 110 and has a height of 60-80 mm, such as 72 mm.

In this embodiment, the two or more installation holes 112 are arranged in an array manner, an inter-row distance D1 between the two or more installation holes 112 is 50-70 mm, such as 60 mm, and an inter-column distance D2 between the two or more installation holes 112 is 20-40 mm, such as 30 mm.

Figure 7:
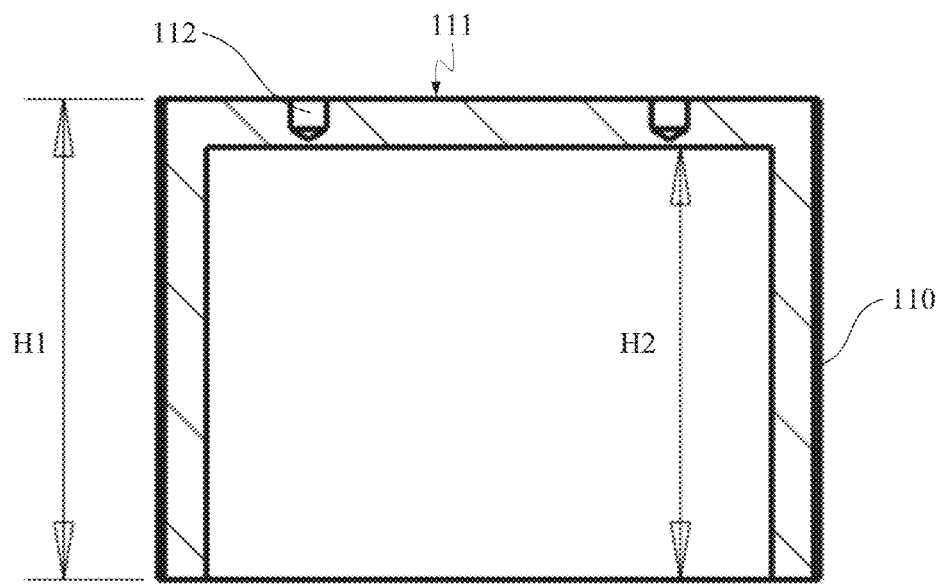
FIG. 7 is a sectional view in the direction of MM in FIG. 6.
Figure 8:
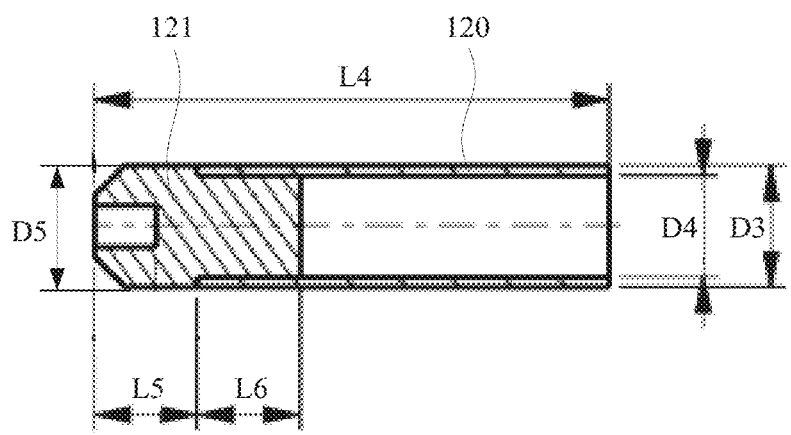
FIG. 8 is a sectional view of a support prop of the precision detection device for a surgical robot positioning system according to an embodiment of the invention.

FIG. 7 is a sectional view of the prop 120 of the precision detection device 100 for a surgical robot 300 positioning system, wherein LA is the length of the prop 120. In this embodiment, the props 120 are perpendicular to the installation surface 111, and the two or more props 120 includes a first set of props 120 arranged in pair, a second set of props 120 arranged in pair, and a third set of props 120 arranged in pair, namely, each set include two props 120. The props in the first set respectively have a length L4 of 80-90 mm and a length L4 of 20-30 mm, the props in the second set respectively have a length L4 of 45-55 mm and a length L4 of 20-30 mm, and the props in the third set respectively have a length L4 of 20-30 mm and a length L4 of 20-30 mm. For instance, the props 120 in the first set respectively have a length L4 of 85 mm and a length L4 of 25 mm, the props 120 in the second set respectively have a length L4 of 50 mm and a length L4 of 25 mm, and the props 120 in the third set respectively have a length L4 of 25 mm and a length L4 of 25 mm. In other embodiments, the length of the props 120 can be set to other values.

In this embodiment the installation holes 112 have a diameter of 5-8 mm, such as 6 mm, and a depth of 4-6 mm, such as 5 mm. The props 120 are hollow props. Connectors 121 matched with the installation holes 112 are arranged at one ends of the posts 120. The props 120 have an outer diameter D3 of 5-8 mm, such as 6 mm, and an inner diameter D4 of 4-7 mm, such as 5 mm. The connectors 121 have an outer diameter D5 of 5-8 mm, such as 6 mm, and extend outwards from one ends of the props 120 by a length L5 of 5-8 mm, such as 5 mm. The connectors 121 can be partially embedded in the props 120 by a length L6 of 5-8 mm, such as 5 mm.

The embodiments mentioned above do not illustrate all details of the invention, and the invention should not be limited to the above embodiments. Obviously, various modifications and variations can be made with reference to the above description. These embodiments specifically described in this description are used to better explain the principle and actual application of the invention, so that those skilled in the art can easily implement the invention and make modifications based on the invention. The invention is limited by the claims and the scope and equivalents thereof.

What is claimed is:

1. A computer-implemented precision detection method for a surgical robot positioning system, used for detecting the precision of the surgical robot positioning system on a computer comprising a processor, the method comprising:
   acquiring, by the processor, spatial position coordinates of a first detection point and a second detection point;
   acquiring, by the processor, information of a central axis of a test probe; and
   calculating, by the processor, a first distance from the first detection point to the central axis and a second distance from the second detection point to the central axis;
   wherein, the test probe is at an execution end of a surgical robot, the surgical robot is moving to a planned path, and the planed path is formed based on the first detection point and the second detection point,
   wherein the acquiring information of the central axis of the test probe comprises:
   acquiring, by the processor, a scan image of the first detection point and the second detection point in the surgical robot positioning system; and
   forming, by the processor, the planned path by taking imaging points of the first detection point and the second detection point in the scan image respectively as an In point and an Out point;
   wherein, the In point is a start point of the planned path and the Out point is an end point of the planned path.

2. The method according to claim 1, wherein the acquiring spatial position coordinates of a first detection point and a second detection point comprises: acquiring, by the processor, the spatial position coordinates of the first detection point and the second detection point measured with a three-dimensional measurement instrument.

3. The method according to claim 1, further comprising: carrying out, by the processor, image registration on the scan image and the first and second detection points after the scan image has been acquired.

4. The method according to claim 3, further comprising: acquiring, by the processor, position information of the first detection point and the second detection point at a certain frequency, and correspondingly adjusting the planned path when the position information of the detection points changes.

5. The method according to claim 1, wherein the central axis information of the test probe at the execution end of the surgical robot is measured through a three-dimensional measurement instrument.

6. The method according to claim 1, wherein the central axis information of the test probe at the execution end of the surgical robot is measured through the following steps:
   acquiring, by the processor, coordinates of at least two fitting points on the central axis of the test probe; and
   fitting, by the processor, the coordinates of the at least two fitting points to obtain a position of the central axis of the test probe.

7. The method according to claim 6, wherein the acquiring coordinates of at least two fitting points on the central axis of the test probe comprises: taking, by the processor, central holes at two ends of the test probe respectively as a first fitting point and a second fitting point to obtain a coordinate $P1(x_1, y_1, z_1)$ of the first fitting point and a coordinate $P2(x_2, y_2, z_2)$ of the second fitting point.

8. The method according to claim 7, wherein the coordinate of the first detection point is $Xa(x_a, y_a, z_a)$, and the coordinate of the second detection point is $Xb(x_b, y_b, z_b)$; and
   the calculating a first distance from the first detection point to the central axis and a second distance from the second detection point to the central axis comprises: calculating, by the processor, the first distance and the second distance according to the following formula:

$$L_i = \sqrt{[(x_1 - x_i) + (x_2 - x_1)t]^2 + [(y_1 - y_i) + (y_2 - y_1)t]^2 + [(z_1 - z_i) + (z_2 - z_1)t]^2},$$

$$\text{wherein, } t = -\frac{(x_1 - x_i)(x_2 - x_1) + (y_1 - y_i)(y_2 - y_1) + (z_1 - z_i)(z_2 - z_1)}{(x_2 - x_1)^2 + (y_2 - y_1)^2 + (z_2 - z_1)^2};$$

i is a or b;
La is the first distance, and Lb is the second distance.

9. The method according to claim 1, further comprising:
   acquiring, by the processor, two detection points from a plurality of detection points excluding the first detection point and the second detection point to carry out precision detection again.

* * * * *